(12) United States Patent
Pradhan et al.

(10) Patent No.: US 8,051,020 B2
(45) Date of Patent: Nov. 1, 2011

(54) BASE OIL PROPERTIES EXPERT SYSTEM

(75) Inventors: Ajit Ramchandra Pradhan, Walnut Creek, CA (US); John M. Rosenbaum, Richmond, CA (US); Nancy J. Bertrand, Lafayette, CA (US); David C. Kramer, San Anselmo, CA (US); Allan G. Hee, Albany, CA (US); Max I. Chang, Singapore (SG)

(73) Assignee: Chevron U.S.A. Inc., San Ramon, CA (US)

( * ) Notice: Subject to any disclaimer, the term of this patent is extended or adjusted under 35 U.S.C. 154(b) by 541 days.

(21) Appl. No.: 12/336,636

(22) Filed: Dec. 17, 2008

(65) Prior Publication Data

US 2010/0049681 A1 Feb. 25, 2010

Related U.S. Application Data

(60) Provisional application No. 61/015,490, filed on Dec. 20, 2007.

(51) Int. Cl.
*G06E 1/00* (2006.01)
*G06E 3/00* (2006.01)
*G06F 15/18* (2006.01)
*G06G 7/00* (2006.01)
*G01N 11/00* (2006.01)

(52) U.S. Cl. ......................................... 706/21; 73/54.01
(58) Field of Classification Search ...................... 706/21
See application file for complete search history.

(56) References Cited

U.S. PATENT DOCUMENTS

2006/0199743 A1* 9/2006 Rosenbaum et al. ......... 508/110

OTHER PUBLICATIONS

Barman et al "Petroleum and Coal" Analytical Chemistry. 2001. [Online] Downloaded Jul. 27, 2011 http://www.ucalgary.ca/files/mehrotra/2001-Barman-Cebolla-Mehrotra-Mansfield-AnalChem.pdf.*

Pensado, A.S., M.J.P. Comunas, and J. Fernandez. "Relationship between Viscosity Coefficients and Volumetric Properties: Measurements and MOdeling from Pentaerythritol Esters" Ind. Eng. Chem. 2006. [Online] Downloaded Jul. 26, 2011. http://pubs.acs.org/doi/pdf/10.1021/ie0606035.*

(Continued)

*Primary Examiner* — Jeffrey A Gaffin
*Assistant Examiner* — Ben Rifkin
(74) *Attorney, Agent, or Firm* — Timothy J. Hadlock

(57) ABSTRACT

A method for predicting properties of lubricant base oil blends, comprising the steps of generating an NMR spectrum, HPLC-UV spectrum, and FIMS spectrum of a sample of a blend of at least two lubricant base oils and determining at least one composite structural molecular parameter of the sample from said spectrums. SIMDIST and HPO analyses of the sample are then generated in order to determine a composite boiling point distribution and molecular weight of the sample from such analysis. A composite structural molecular parameter is applied, and the composite boiling point distribution and the composite molecular weight to a trained neural network is trained to correlate with the composite structural molecular parameter composite boiling point distribution and the composite molecular weight so as to predict composite properties of the sample. The properties comprise Kinematic Viscosity at 40 C, Kinematic Viscosity at 100 C, Viscosity Index, Cloud Point, and Oxidation Performance.

3 Claims, 10 Drawing Sheets

Statistical Model Development for the Prediction of Base Oil Properties

OTHER PUBLICATIONS

Sharma, Brajendra and Arthur Stipanovic. "Pressure Viscosity Coefficient of Lubricant Base Oils as Estimated by Nuclear Magnetic Resonance Spectroscopy" Ind. Eng. Chem. Res. 2002. [Online] Downloaded Jul. 26, 2011 http://pubs.acs.org/doi/pdf/10.1021/ie020360q.*

Adhvaryu, A. et al., "Application of Quantitative [13]C Nuclear Magnetic Resonance Spectroscopy to the Characterisation of Solvent-Refined Aromatic-Rich Lubricant Base Oils", Lubrication Science, Nov. 2002, pp. 3-16, vol. 15, No. 1, Leaf Coppin Publishing Co., GB.

Sharma, B.K. et al., "Pulsed Field Gradient NMR Spectroscopy: Applications in Determining the Pressure Viscosity Coefficient and Low-Temperature Flow Properties of Lubricant Base Oils", Industrial and Engineering Chemistry Research, Apr. 2, 2003, pp. 1522-1529, vol. 42, No. 7, American Chemical Society, U.S.

Basu, B. et al., "Prediction of Oxidation Stability of Inhibited Base Oils From Chemical Composition Using an Artificial Neural Network (ANN)", Lubrication Science, Feb. 1998, pp. 121-134, vol. 10, No. 2, Feb Leaf Coppin Publ. Ltd.

Shea, T.M. et al., "Modeling Base Oil Properties Using NMR Spectroscopy and Neural Networks", Tribology Transactions, Jul. 2003, pp. 296-302, vol. 46, No. 3, Society of Tribologists and Lubrication Engineers, U.S.

* cited by examiner

Prediction of Pour Point
(with new MW)

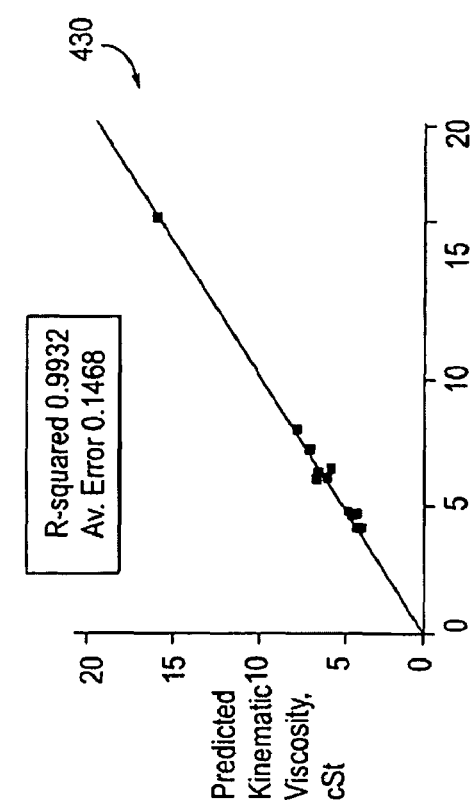

BASE OIL PROPERTIES EXPERT SYSTEM

COPYRIGHT NOTICE AND AUTHORIZATION

This patent document contains material which is subject to copyright protection.

© Copyright 2007. Chevron U.S.A. Inc. All rights reserved.

With respect to this material which is subject to copyright protection. The owner, Chevron U.S.A., Inc., has no objection to the facsimile reproduction by any one of the patent disclosure, as it appears in the Patent and Trademark Office patent files or records of any country, but otherwise reserves all rights whatsoever.

FIELD OF THE INVENTION

The invention relates to computer-based expert system for predicting properties of base oils.

BACKGROUND OF THE INVENTION

Currently, there is a need in the lubrication industry for an improved method that would allow prediction of base oil properties and more specifically, allow the formulation of base stock and lubricants with specific properties. At present, there is no method available that would allow the prediction of base oil properties. Base oils are presently characterized by ASTM, API, and DIN methods. These methods are time consuming and require large amount of sample quantity. There have been efforts to predict base oil properties from structural information obtained from NMR spectroscopy. For example, Shea et al. (1) use the NMR spectroscopy and Neural network for this purpose. B. K. Sharma et al. (2) correlated pressure viscosity coefficient of Lubricant Base oils with structural parameters obtained from NMR Spectroscopy. Gatto et al. (3) correlated the physical properties and antioxidant response of hydrocracked base oils and polyalphaolefins to chemical composition determined by mass spectrometry. However, most of these studies are limited to the specific set of samples or specific analytical technique. There has been no reported knowledge using various analytical techniques, in addition to NMR, to improve prediction capability of the Base Oil Model. More importantly, there is no method available that would allow the formulation of base oil and lubricants with specific properties.

The Base Oil Predictor preferably has a user-friendly interface. One could select from the menu up to, e.g., four base oils from, e.g., about 40 base oils available at the U.S. blending units. With single click it would be possible to predict base oil properties of the blends that includes VI, Vis40, Vis100, OxBN, Pour Point, Cloud Point and NOACK Volatility. In a preferred embodiment, it incorporates more base oils.

Testing is done by: testing the model for the blends with known properties, preparing a blend of two, three and four base oils in known composition and submit the blend for the above test as well as for the NMR analysis.

Various studies (1-3) reported in the literature recognize that most of the bulk properties of base oils result from hydrocarbon type distribution in the base oil. During last 60 years, NMR Spectroscopy has become one of the major analytical tools for the structural determination of hydrocarbons. Other techniques used for the characterization of the hydrocarbons are MS and HPLC. In the present invention, structural parameters of the base oil are determined by these analytical techniques such as NMR, HPLC-UV and FIMS. Base oils are further characterized using SIMDIST and VPO to get the boiling point distribution and molecular weight respectively. These structural parameters are then modeled against the experimentally observed physical properties of the initial set of base oils. An artificial neural network is used to develop such a model. A number of properties that could be modeled include, but not limited to, Kinematic Viscosity at 40° C., Kinematic Viscosity at 100° C., Viscosity Index, Pour Point, Cloud Point, Oxidation Performance, etc.

As part of the initial study, we selected 20 base oil samples from Group I, II and III. For the characterization by NMR spectroscopy, each base oil is characterized using a quantitative 13C NMR technique. Once a spectrum is acquired, integrals are recorded over several regions to differentiate various types of carbons. All these samples were further characterized using analytical techniques mentioned above and the structural parameters determined using these techniques is presented in table 1. These structural parameters are modeled using NeuroShell predictor Release 2.2 software from Ward System Group. All models were constructed using a back-propagation algorithm. A separate and distinct model is constructed for each property. After a model is developed a correlation coefficient is obtained. A comparison of the expected values and estimated values for the Viscosity Index, Kinematic Viscosity at 40° C., Kinematic Viscosity at 100° C., Pour Point, and Oxidation Performance is presented in Tables 2, 3, 4 and 5 respectively. The correlation coefficient obtained for various models suggest that the structural features derived from various analytical techniques accurately model various physical properties of the base oil. This technique has a value in 1) predicting base oil blends that will match desired performance, 2) streamline in handling base oil changes, 3) identify synthetic target molecules to improve performance, 4) reduce the amount of laboratory testing and 5) design new catalyst to maximize key attributes. More work is underway to improve the model further and to include base oils with more diverse properties.

SUMMARY OF THE INVENTION

The invention includes a method of simulating and optimizing qualification testing of lubricating oil products, the method including the following steps: a method for predicting properties of lubricant base oil blends, comprising the steps of generating an NMR spectrum, HPLC-UV spectrum, and FIMS spectrum of a sample of a blend of at least two lubricant base oils and determining at least one composite structural molecular parameter of the sample from said spectrums. SIMDIST and HPO analyses of the sample are then generated in order to determine a composite boiling point distribution and molecular weight of the sample from such analysis. A composite structural molecular parameter is applied, and the composite boiling point distribution and the composite molecular weight to a trained neural network is trained to correlate with the composite structural molecular parameter composite boiling point distribution and the composite molecular weight so as to predict composite properties of the sample. The properties comprise Kinematic Viscosity at 40 C, Kinematic Viscosity at 100 C, Viscosity Index, Cloud Point, and Oxidation Performance.

These and other features and advantages of the present invention will be made more apparent through a consideration of the following detailed description of a preferred embodiment of the invention. In the course of this description, frequent reference will be made to the attached drawings.

BRIEF DESCRIPTION OF THE DRAWINGS

FIG. 4A depicts in one embodiment illustrative example a graphical representation of the correlation between the predicted and actual viscosity index of a base oil using the method of the invention.

FIG. 4B depicts in one embodiment illustrative example a graphical representation of the correlation between the predicted and actual kinematic viscosity of a base oil using the method of the invention.

FIG. 4C depicts in one embodiment illustrative example a graphical representation of the correlation between the predicted and actual kinematic viscosity of a base oil using the method of the invention.

FIG. 4D depicts in one embodiment illustrative example a graphical representation of the correlation between the predicted and actual pour point of a base oil using the method of the invention.

DETAILED DESCRIPTION OF THE DRAWINGS AND PREFERRED EMBODIMENTS

Figure 1A:
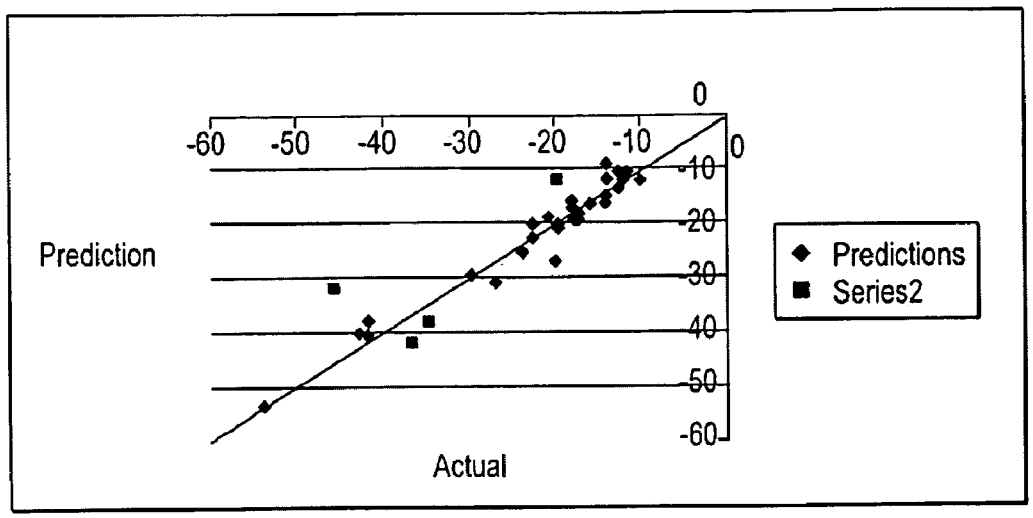
FIG. 1A depicts in one embodiment illustrative example a graphical representation of the correlation between the predicted and actual pour point of a base oil using a previously known model.

Various studies (1-3) reported in the literature recognize that most of the bulk properties of base oils result from hydrocarbon type distribution in the base oil. During last 60 years, NMR Spectroscopy has become one of the major analytical tools for the structural determination of hydrocarbons. Other techniques used for the characterization of the hydrocarbons are MS and HPLC. In the present invention, structural parameters of the base oil are determined by these analytical techniques such as NMR, HPLC-UV and FIMS.

Base oils are further characterized using SIMDIST and VPO to get the boiling point distribution and molecular weight respectively. These structural parameters are then modeled against the experimentally observed physical properties of the initial set of base oils. An artificial neural network is used to develop such a model. A number of properties that could be modeled include, but not limited to, Kinematic Viscosity at 40° C., Kinematic Viscosity at 100° C., Viscosity Index, Pour Point, Cloud Point, Oxidation Performance, etc.

As part of the initial study, we selected 20 base oil samples from Group I, II and III. For the characterization by NMR spectroscopy, each base oil is characterized using a quantitative 13C NMR technique. Once a spectrum is acquired, integrals are recorded over several regions to differentiate various types of carbons. All these samples were further characterized using analytical techniques mentioned above and the structural parameters determined using these techniques is presented in table 1. These structural parameters are modeled using NeuroShell predictor Release 2.2 software from Ward System Group. All models were constructed using a back-propagation algorithm. A separate and distinct model is constructed for each property.

After a model is developed a correlation coefficient is obtained. A comparison of the expected values and estimated values for the Viscosity Index, Kinematic Viscosity at 40° C., Kinematic Viscosity at 100° C., Pour Point, and Oxidation Performance is presented in Tables 2, 3, 4 and 5 respectively. The correlation coefficient obtained for various models suggest that the structural features derived from various analytical techniques accurately model various physical properties of the base oil.

This technique has a value in 1) predicting base oil blends that will match desired performance, 2) streamline in handling base oil changes, 3) identify synthetic target molecules to improve performance, 4) reduce the amount of laboratory testing and 5) design new catalyst to maximize key attributes. More work is underway to improve the model further and to include base oils with more diverse properties.

A. Introduction

The following discussion and figures include a general description of a suitable computing environment in which the invention may be implemented. While the invention may be described in the general context of a system and an application program that runs on an operating system in conjunction with general purpose computers, an internet, and web application, and email servers and clients, those skilled in the art will recognize that the invention also may be implemented in combination with other program modules. Generally, program modules include routines, programs, components, data structures, etc. that performs particular tasks or implement particular abstract data types.

Moreover, those skilled in the art will appreciate that the invention may be practiced with other computer system configurations, including hand-held devices, multiprocessor systems, microprocessor-based or programmable consumer electronics, minicomputers/servers, workstations, mainframe computers, and the like.

The invention may also be practiced in distributed computing environments where tasks are performed by remote processing devices that are linked through a communications network. In a distributed computing environment, program modules may be located in both local and remote memory storage devices.

Then invention generally relates to a simulation system for. The process aspects of the invention are a series of process steps utilizing, in whole or in part, the system herein and variations thereof. As would be clear to one skilled in the art, the process steps can be embodied in part as code for a computer program for operation on a conventional programmed digital computer, such as a client and server. The program code can be embodied as a computer program on a computer-readable storage medium or as a computer data signal in a carrier wave transmitted over a network.

B. Illustrative Benefits of the Invention

The System helps solve the following problems which relate to

C. Illustrative Implementation Environment

An illustrative implementation environment includes: a Java virtual machine, (e.g., JDK 1.3) to support all Java software components. All System components are optionally written in full Java, except for external libraries. A web server (e.g., Apache) to interpret the http code generated by the JSP pages within the System pseudo-component GUI. A servlet engine (e.g., Resin or Tomcat) to execute the Java Server Pages of the System pseudo-component GUI. A database (e.g., ORACLE) that handles all persistent data used within the System.

Actual access to DATA within the System is taken care of by a unique component (DAT), and this access is performed using the JDBC API. Third parties software components or libraries such as STORM™ (from software vendor Elseware) for neural networks and HUGIN™ (from software vendor HUGIN) for Bayesian networks and Blaze Advisor™ (from software vendor Fair Isaac) as code of practice rule engine. An external Extract/Transform/Load ("ETL") procedure, built, e.g., with Informatica brand software, is in charge of filling the System database with data extracted and transformed from past physical qualification tests databases and other sources. The ETL tool is used to extract data from one or more source DB, transform the data and load it on a target DB.

D. Algorithms

Suitable algorithms include Bayesian and Neural Networks. Details on each can be found in the publications in the field.

E. Overview of System Architecture

The functional architecture of the System is summarized in the picture below. the System is comprised of five main functional components: Data Representation (also called Data Collapsing), Model Building, Model Execution, Compliance Evaluation, and Simulation. These components do not necessarily correspond to a software module depending on how the System is implemented. For instance, the data collapsing function may optionally be used in several software modules in the System. This decomposition is the most appropriate to understand how the System works, without going into potential implementation details.

F. Program Simulation

G. Detailed Description of the Figures

Figure 1B:
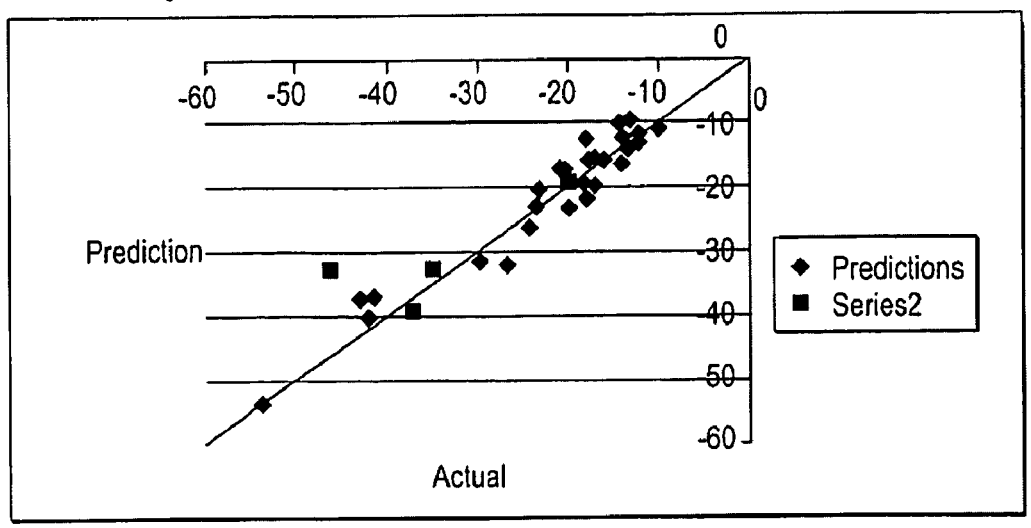
FIG. 1B depicts in one embodiment illustrative example a graphical representation of the correlation between the predicted and actual pour point of a base oil using the method of the invention.
Figure 2:
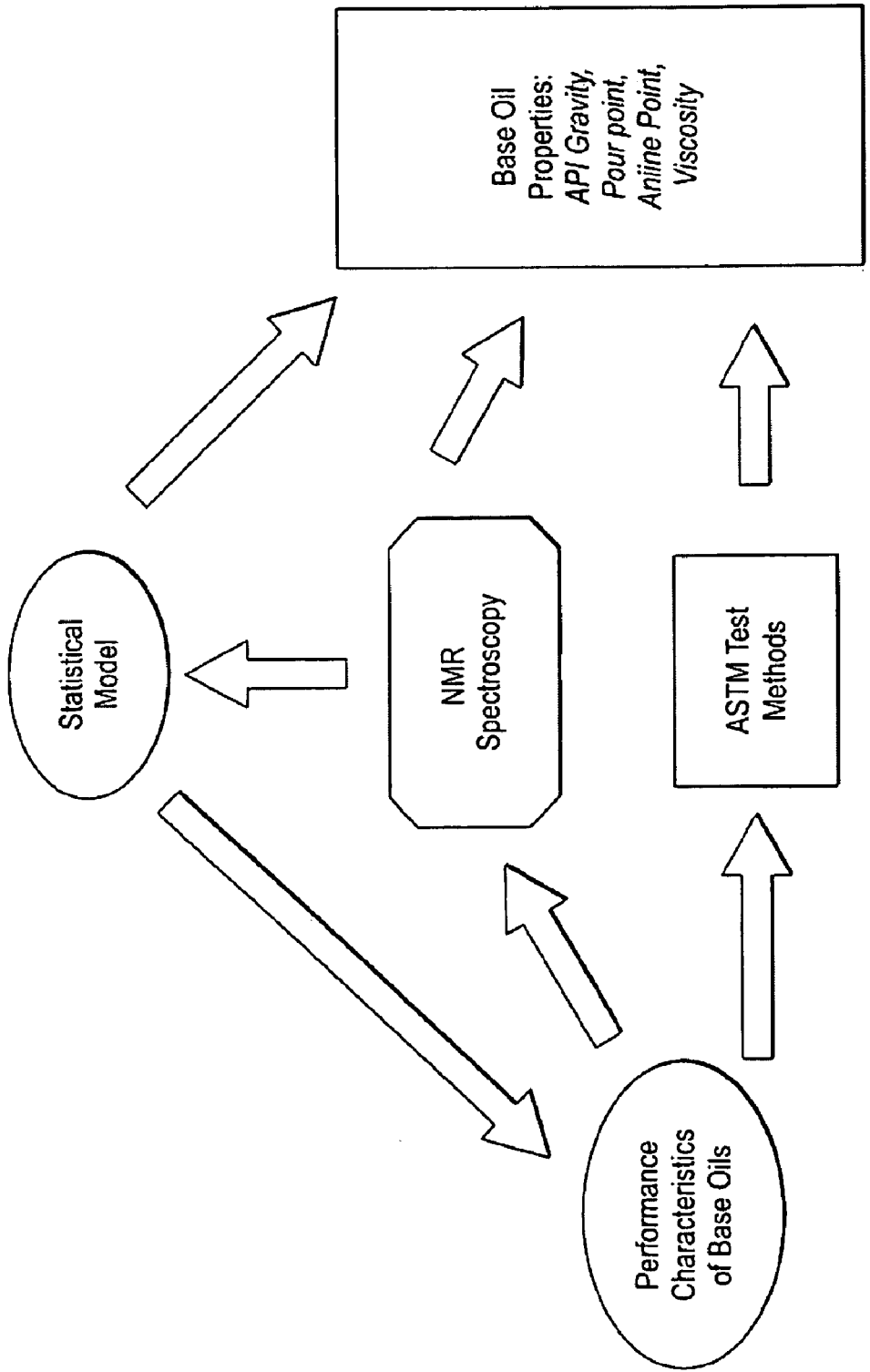
FIG. 2 depicts in one embodiment a schematic system diagram of the invention.

The invention and exemplary implementations thereof will now be described with reference to the figures. FIG. 1 depicts in one embodiment a schematic system diagram for the invention. Inputs from.

Final output of the system includes.

The invention may be built to operate on any conventional computer platform, but preferably is a web-based application accessible by any authorized user having a web browser connected to the Internet or company-internal Intra-net on which an application server containing the invention resides.

The invention may be constructed using conventional software engineering methods. Potential users of the invention will be. Utilizing the system of the invention, from within one piece of software.

Figure 3:
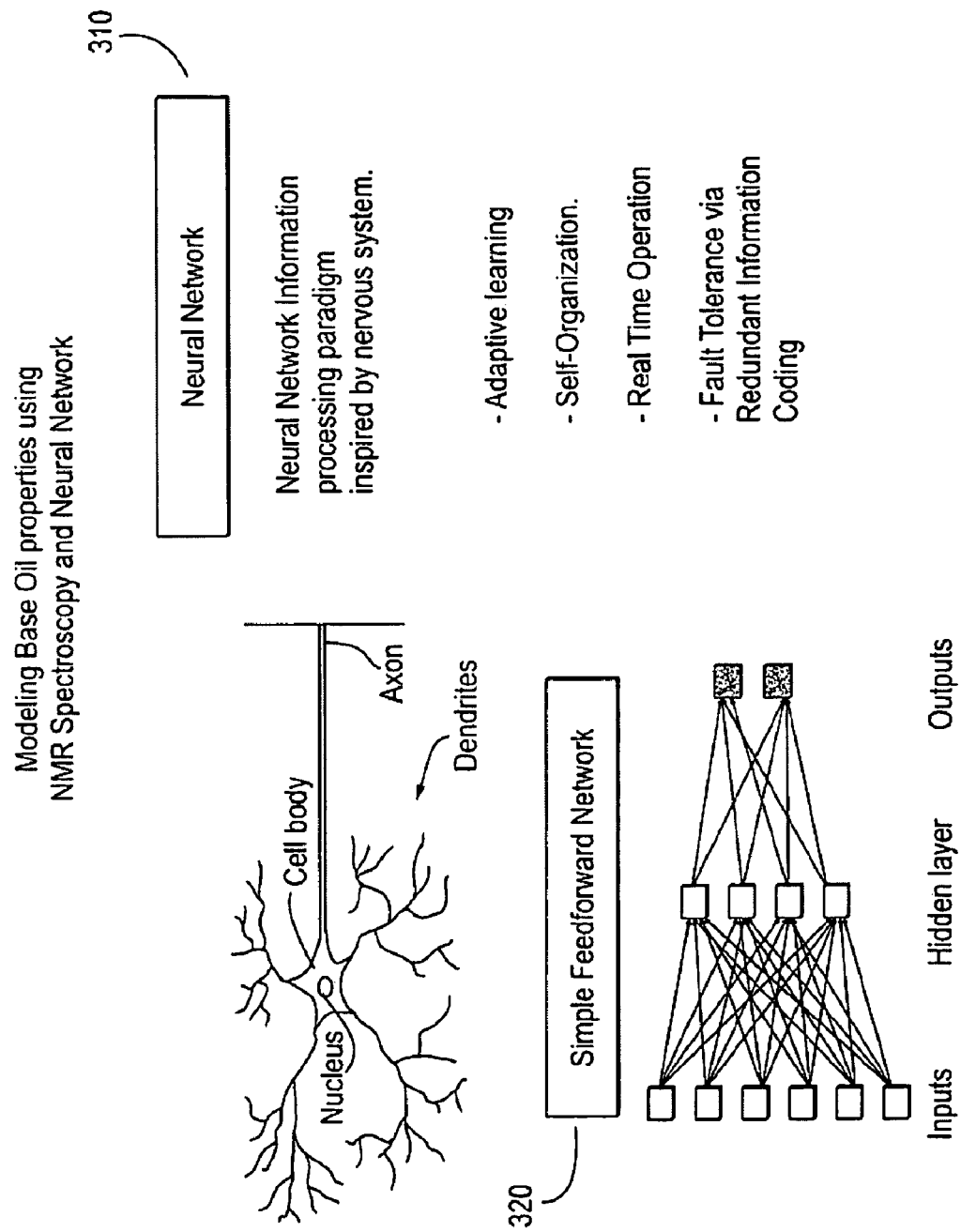
FIG. 3 depicts in one embodiment a schematic system diagram of the invention.

FIG. 3 depicts in one embodiment a schematic layer-view system diagram for one illustrative implementation of the invention. The layers are Client layer 300, Presentation Server layer 310, Application Server layer 330, Data Server layer 370, and Production Data Server layer 380. Client layer 300 includes Navigator 305 comprising a user interface, preferably a graphical user interface ("GUI"), optionally a web browser. Presentation Server layer 310 includes GUI (optionally Java Server Pages) 315 operatively connected to Navigator 305, GUI (optionally powered Java Server Pages) 315, operatively connected to System QUI (optionally a Java Package) 320, operatively connected to Reporting (optionally a Java component) 325.

Application Server layer 330 includes Model Builder (optionally a Java Component) 335 operatively connected to each of the following: Bayesian networks software (e.g., Hugin brand) (optionally an external Java API) 340, neural networks software (e.g., Storm brand) (optionally an external Java API), and Data Management (optionally a Java component) 350. Data Management 350 is operatively connected to both System Foundation Package (optionally a Java Package) 355.

The term directory as used here is by way of example only and is intended to indicate any available programming construct or other methodology for organizing data, files, or records. Higher levels of the directory include Common Workspace objects 405 and User Workspaces objects 410. Under each respective workspace are Oils objects 415, Components objects 420, Program objects 425, and Variant objects 430. Under Program objects 425, are Strategy objects 435. Load Common Objects on System Start module 445 and Save Objects Upon Request module 440 provide the functions indicated by the name of each module.

Figure 5:
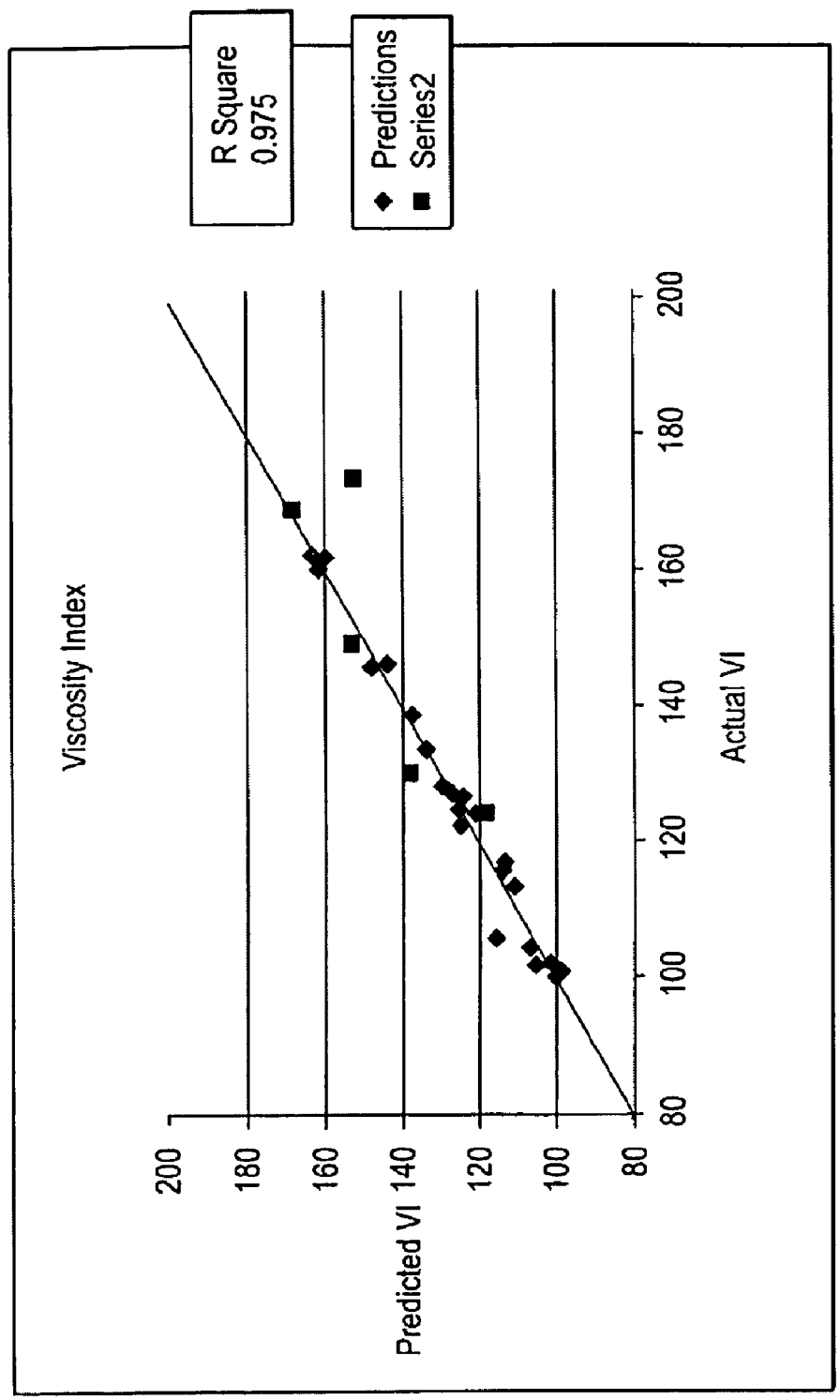
FIG. 5 depicts in one embodiment illustrative example a graphical representation of the correlation between the predicted and actual viscosity index of a base oil using the method of the invention.

FIG. 5 depicts in one embodiment a more detailed schematic system diagram of the user interface component for one illustrative implementation of the invention.

FIG. 5 repeats modules shown in FIG. 1, 3, or 4 and additionally shows point of interface between various users and the system. The roles of the different users are also listed. The roles of the Data administrator 505 include Maintain database and Maintain Codes of Practice. The Data administrator 505 interfaces with the system via ETL Procedure module 385.

Figure 6A:
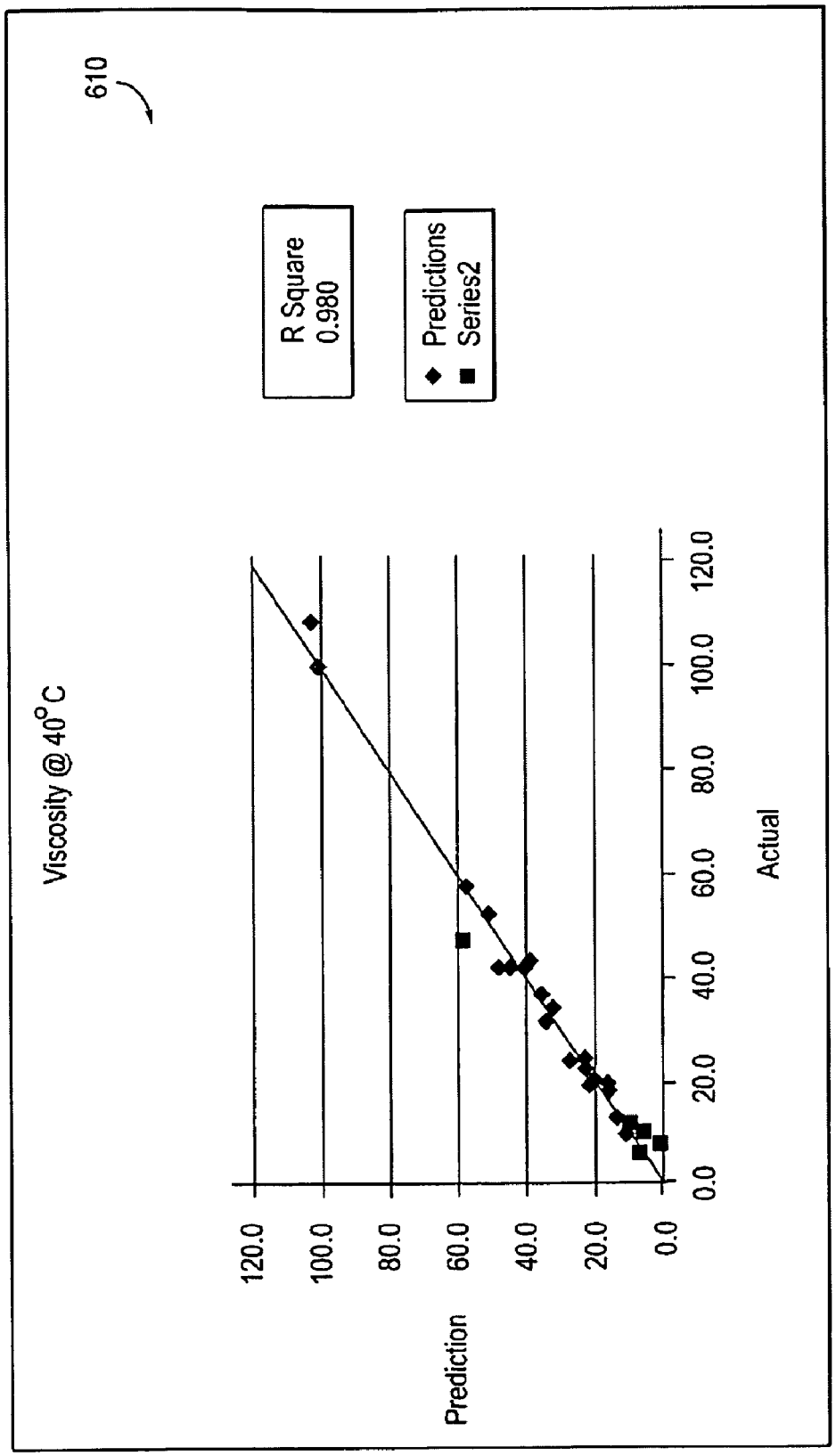
FIG. 6A depicts in one embodiment illustrative example a graphical representation of the correlation between the predicted and actual viscosity at 40 degrees Celsius of a base oil using the method of the invention.
Figure 6B:
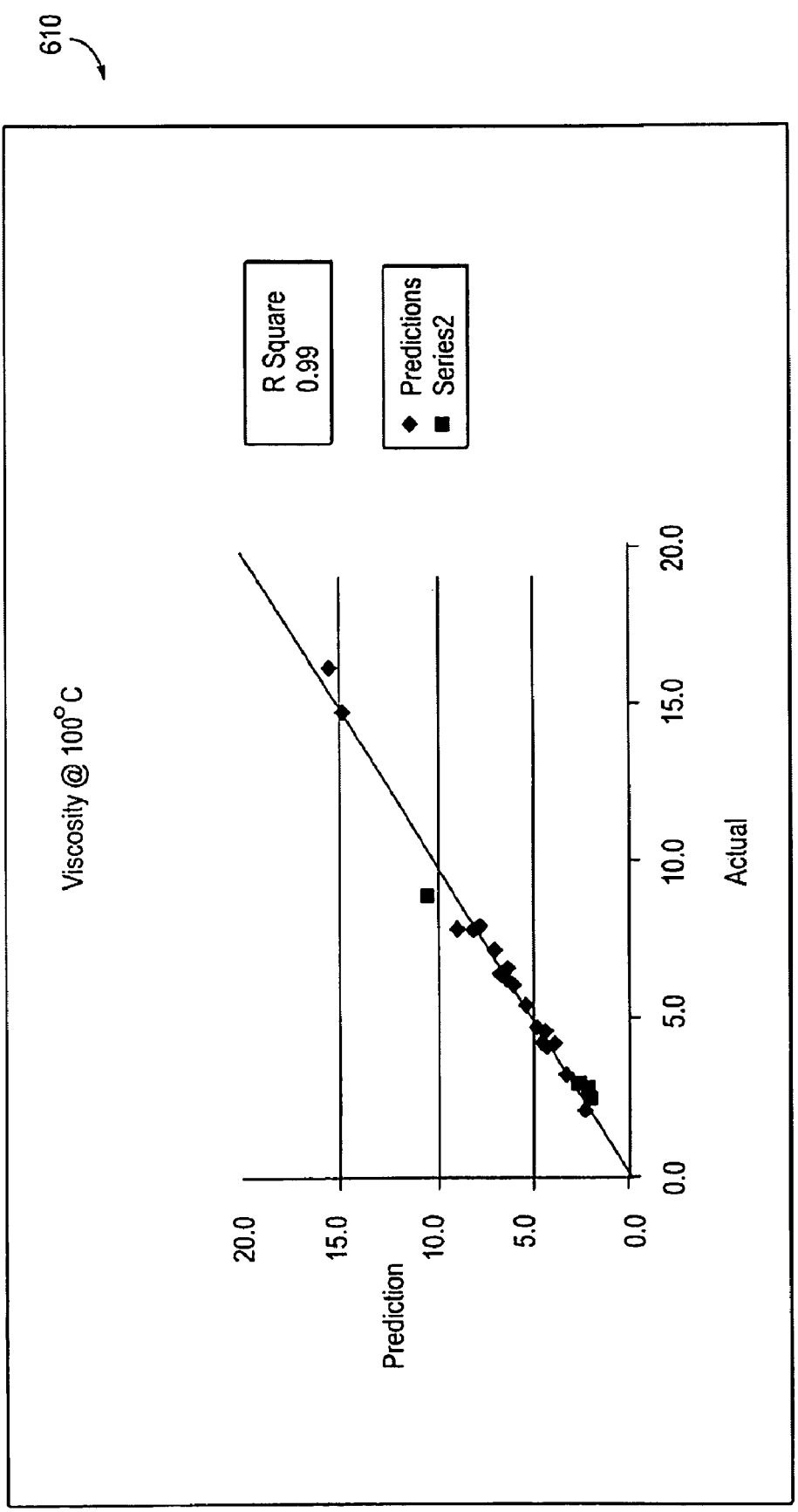
FIG. 6B depicts in one embodiment illustrative example a graphical representation of the correlation between the predicted and actual viscosity at 100 degrees Celsius of a base oil using the method of the invention.
Figure 7:
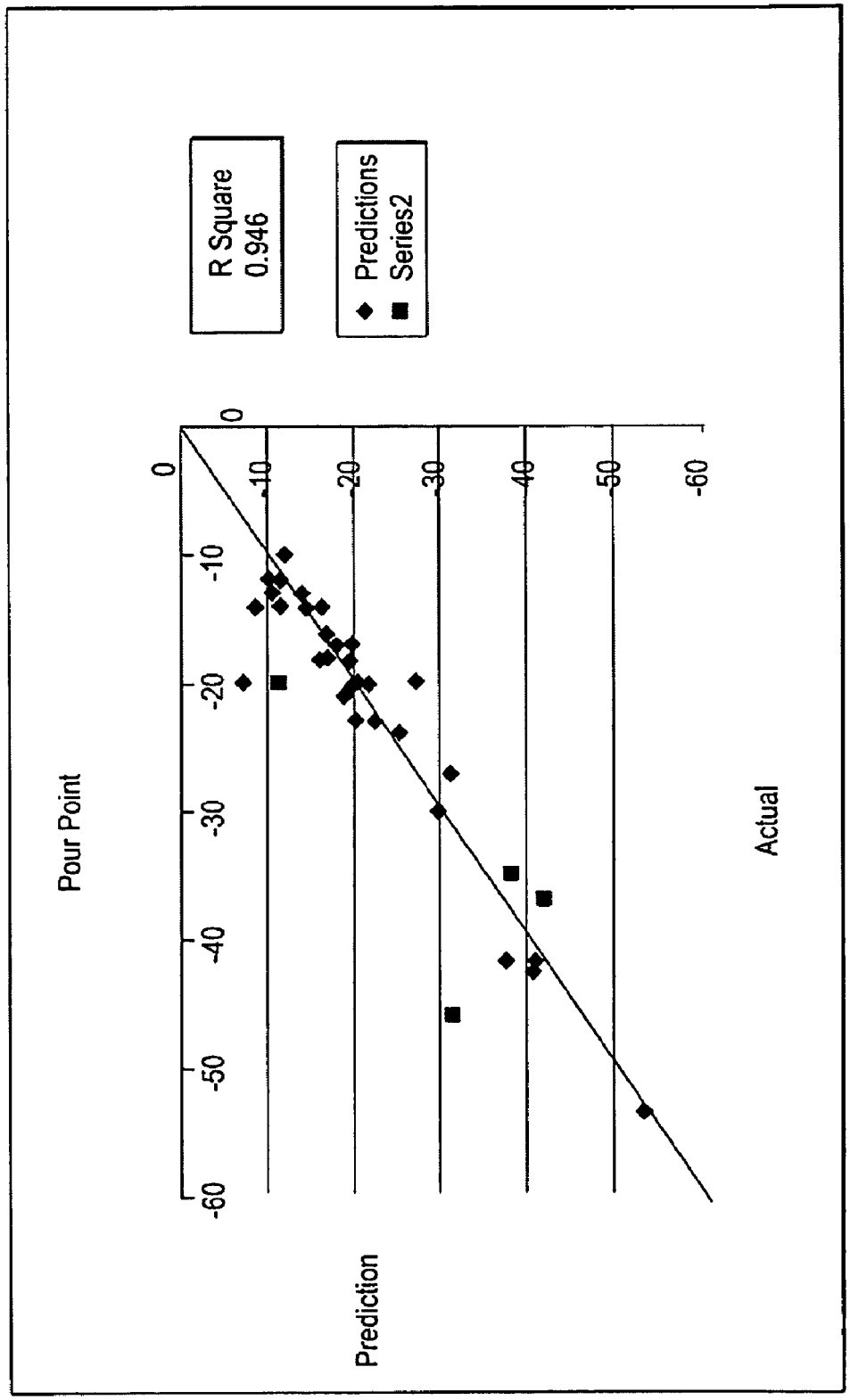
FIG. 7 depicts in one embodiment illustrative example a graphical representation of the correlation between the predicted and actual pour point of a base oil using the method of the invention.
Figure 8:
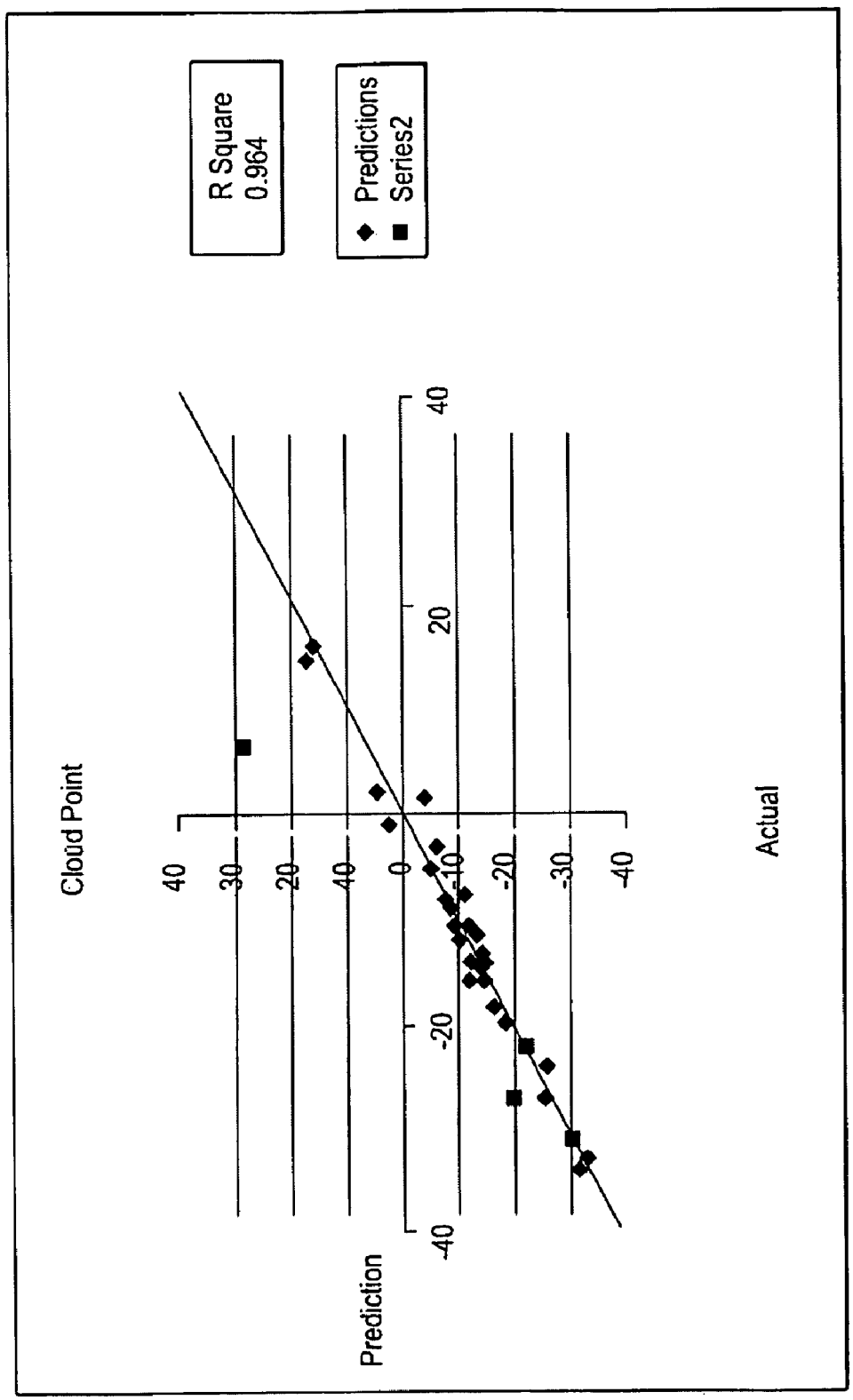
FIG. 8 depicts in one embodiment illustrative example a graphical representation of the correlation between the predicted and actual cloud point of a base oil using the method of the invention.

FIG. 6 depicts in one embodiment a schematic process flow diagram with a logical view of the data for one illustrative implementation of the invention.

Figure 9:
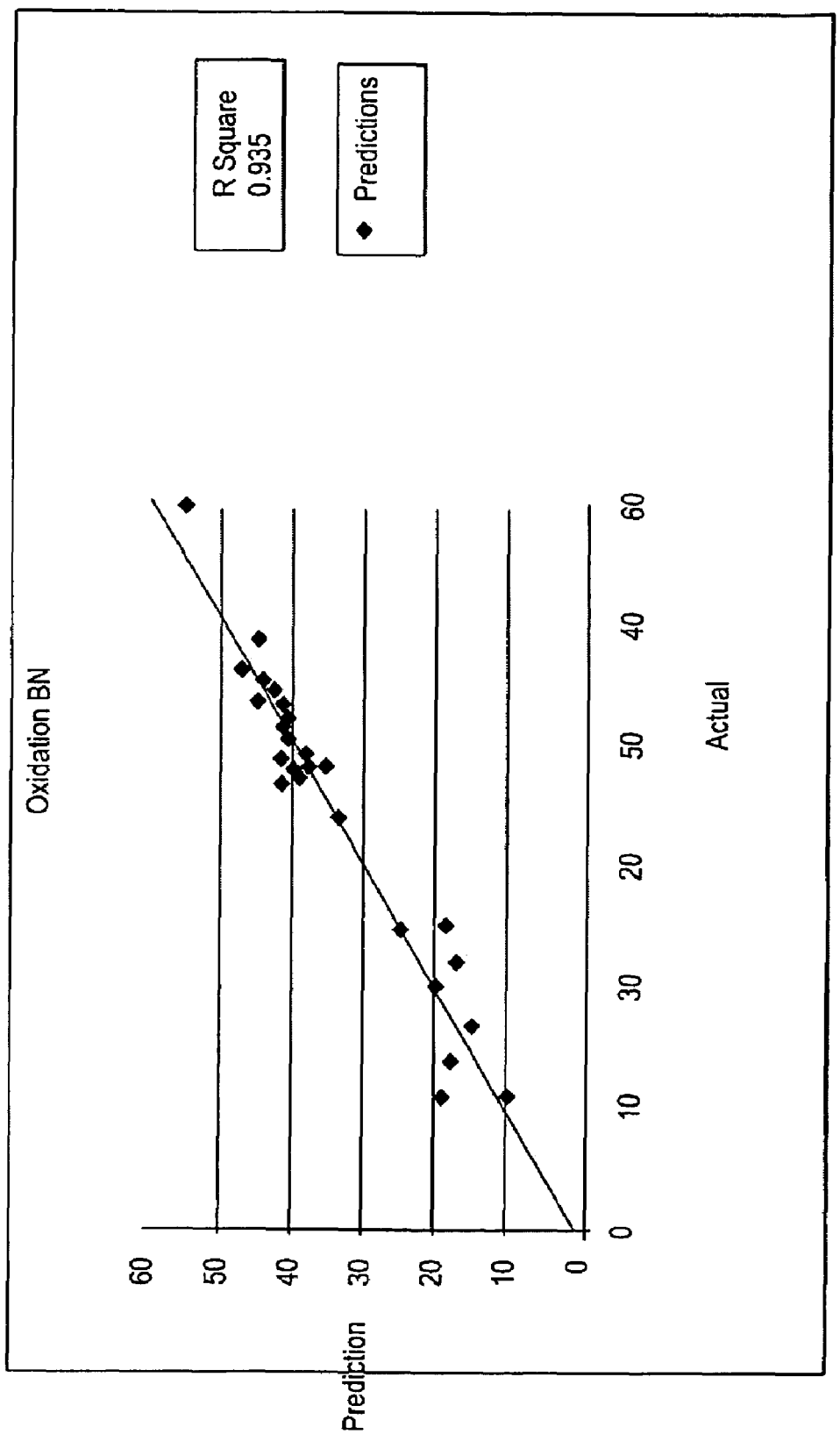
FIG. 9 depicts in one embodiment illustrative example a graphical representation of the correlation between the predicted and actual oxidation BN of a base oil using the method of the invention.

FIG. 9 depicts process logic flow for general strategy execution.

FIG. 10 depicts process logic flow for individual line processing.

H. Illustrative Embodiments

TABLE 1

Input Structural Parameters for the Modeling

| Analytical Technique | Abbreviation | Input Parameter |
|---|---|---|
| NMR | # C | Total number of carbons per molecule |
| | P/sumAlk | Total Methyl/Alkyl Carbons per molecule |
| | P/t-me | terminal methyl |
| | P/2-me | 2-methyl |
| | P/3-me | 3-methyl |
| | P/4-me | 4-methyl |
| | P/5+ me | 5+ methyl |
| | P/adj-me | adjacent methyl |
| | P/int-eth | internal ethyl |
| | P/int-pro | internal propyl |
| | P/sumCH2 | Total Methylene Carbons per molecule |
| | P/ε CH2 | epsilon carbons |
| | P/CH | paraffinic methine (by DEPT) |
| | N/sumC | Total Naphthenic Carbons per Molecule |
| | N/CH2 | naphthenic methylene (by DEPT) |
| | N/CH | naphthenic methine (by DEPT) |
| | A/sumC | Total Aromatic Carbons per Molecule |
| | A/nonsub | non-substituted aromatic |
| | A/bridged | bridged aromatic |
| | A/sub | substituted aromatic |
| | BI | Branching Index |
| | BP | Branching Proximity |
| | FCI | FCI |
| HPLC | HPLC1R | HPLC-UV 1-Ring |
| | HPLC2R | HPLC-UV 2-Ring |
| | HPLC3R | HPLC-UV 3-Ring |
| SIMDIST | TBP/50% | SIMDIST TBP @ 50 wt. %, F |
| FIMS | FIMSa | alkanes by FIMS (area %) |
| | FIMS1u | 1-unsturation by FIMS (area %) |
| | FIMS2u | 2-unsaturation by FIMS (area %) |
| | FIMS3u | 3-unsaturation by FIMS (area %) |

TABLE 2

Actual and Predicted Values of the Viscosity Index

| Sample Code | Actuals | Predictions |
|---|---|---|
| 4R | 126 | 125.5 |
| 5R | 115 | 115.9 |
| 7R | 134 | 133.4 |
| Chevron 100R | 101 | 102.0 |
| Chevron 220R | 104 | 103.1 |
| EHC-45 | 116 | 118.9 |
| EHC-90 | 113 | 108.1 |
| Star 4 | 106 | 105.5 |
| Star 8 | 102 | 102.7 |
| PC VHVI4 | 127 | 125.5 |
| PC VHVI6 | 129 | 128.2 |
| PC VHVI8 | 126 | 126.7 |
| Pennzoil100 | 100 | 100.2 |
| Pennzoil230 | 101 | 102.1 |
| GBO L | 145 | 144.3 |
| GBO M | 160 | 158.4 |
| GBO H | 161 | 159.9 |
| SCH L | 146 | 149.3 |
| SCH M | 162 | 162.1 |
| SCH H | 161 | 161.2 |
| Visom 4 | 138 | 138.5 |
| Yubase 4 | 122 | 123.2 |
| UCBO 4R | 126 | 126.2 |
| R-squared | | 0.994 |
| Av. Error | | 1.1 |

TABLE 3

Actual and Predicted Values of the Kinematic Viscosity at 40° C., cSt

| Sample Code | Actuals | Predictions |
|---|---|---|
| 4R | 18.63 | 17.9 |
| 5R | 23.77 | 22.3 |
| 7R | 41.62 | 41.0 |
| Chevron 100R | 20.55 | 20.0 |
| Chevron 220R | 41.34 | 42.6 |
| EHC-45 | 23.29 | 23.2 |
| EHC-90 | 36.45 | 39.8 |
| Star 4 | 19.45 | 19.4 |
| Star 8 | 56.98 | 56.8 |
| PC VHVI4 | 21.38 | 22.9 |
| PC VHVI6 | 33.79 | 34.0 |
| PC VHVI8 | 51.79 | 51.0 |
| Pennzoil100 | 20.09 | 19.7 |
| Pennzoil230 | 42.85 | 40.8 |
| GBO L | 17.2 | 19.1 |
| GBO M | 30.5 | 29.1 |
| GBO H | 42.19 | 42.0 |
| SCH L | 17.13 | 16.4 |
| SCH M | 42.35 | 43.6 |
| SCH H | 108.4 | 108.0 |
| Visom 4 | 17.35 | 15.8 |
| Yubase 4 | 18.96 | 20.0 |
| UCBO 4R | 18.63 | 19.1 |
| R-squared | | 0.996 |
| Av. Error | | 1.0 |

TABLE 4

Actual and Predicted Values of the Kinematic Viscosity at 100° C., cSt

| Sample Code | Actuals | Predictions |
|---|---|---|
| 4R | 4.14 | 4.29 |
| 5R | 4.69 | 4.87 |
| 7R | 7.15 | 7.03 |
| Chev100R | 4.14 | 4.05 |
| Chev220R | 6.42 | 6.64 |
| EHC-45 | 4.64 | 4.36 |
| EHC-90 | 6.08 | 6.76 |
| Star 4 | 4.05 | 4.03 |
| Star 8 | 7.84 | 7.92 |
| PC VHVI4 | 4.53 | 4.59 |
| PC VHVI6 | 6.10 | 6.09 |
| PC VHVI8 | 8.06 | 7.85 |
| Pennzoil100 | 4.07 | 4.01 |
| Pennzoil230 | 6.49 | 6.02 |
| GBO L | 4.10 | 4.00 |
| GBO M | 6.24 | 5.96 |
| GBO H | 7.90 | 8.02 |
| SCH L | 4.10 | 4.13 |
| SCH M | 7.93 | 8.19 |
| SCH H | 16.24 | 16.09 |
| R-squared | | 0.993 |
| Av. Error | | 0.15 |

TABLE 5

Actual and Predicted Values of the Pour Point (° C.)

| Sample Code | Actuals | Predictions |
|---|---|---|
| 4R | −18.0 | −18.0 |
| 5R | −17.0 | −16.9 |
| 7R | −18.0 | −18.3 |
| Chev100R | −13.0 | −13.6 |
| Chev220R | −14.0 | −13.7 |
| EHC-45 | −18.0 | −18.0 |
| EHC-90 | −18.0 | −18.2 |
| Star 4 | −21.0 | −21.1 |
| Star 8 | −16.0 | −16.0 |
| PC VHVI4 | −23.0 | −22.9 |
| PC VHVI6 | −12.0 | −12.0 |
| PC VHVI8 | −13.0 | −13.0 |
| Pennzoil100 | −14.0 | −13.7 |
| Pennzoil230 | −14.0 | −13.8 |
| GBO L | −20.0 | −20.6 |
| GBO M | −20.0 | −19.9 |
| GBO H | −14.0 | −13.9 |
| SCH L | −24.0 | −23.9 |
| SCH M | −20.0 | −19.5 |
| SCH H | −10.0 | −10.1 |
| R-squared | | 0.995 |
| Av. Error | | 0.2 |

TABLE 6

Actual and Predicted Values of the Oxidation Stability (Oxidator BX, hrs)

| Sample Code | Actuals | Predictions |
|---|---|---|
| 4R | 21.17 | 21.16 |
| GBO L | 16.89 | 16.88 |
| GBO H | 21.05 | 21.06 |
| Nexbase 3043 | 19.09 | 19.21 |
| Visom 4 | 16.44 | 16.44 |
| Yubase 4 | 21.94 | 21.75 |
| UCBO 4R | 21.17 | 21.24 |
| Yubase 8 | 17.34 | 17.25 |
| Nexbase 3080 | 20.75 | 20.84 |
| R-squared | | 0.998 |
| Av. Error | | 0.06 |

I. Other Implementation Details

1. Terms

The detailed description contained herein is represented partly in terms of processes and symbolic representations of operations by a conventional computer and/or wired or wireless network. The processes and operations performed by the computer include the manipulation of signals by a processor and the maintenance of these signals within data packets and data structures resident in one or more media within memory storage devices. Generally, a "data structure" is an organizational scheme applied to data or an object so that specific operations can be performed upon that data or modules of data so that specific relationships are established between organized parts of the data structure.

A "data packet" is type of data structure having one or more related fields, which are collectively defined as a unit of information transmitted from one device or program module to another. Thus, the symbolic representations of operations are the means used by those skilled in the art of computer programming and computer construction to most effectively convey teachings and discoveries to others skilled in the art.

For the purposes of this discussion, a process is generally conceived to be a sequence of computer-executed steps leading to a desired result. These steps generally require physical manipulations of physical quantities. Usually, though not necessarily, these quantities take the form of electrical, magnetic, or optical signals capable of being stored, transferred, combined, compared, or otherwise manipulated. It is conventional for those skilled in the art to refer to representations of these signals as bits, bytes, words, information, data, packets, nodes, numbers, points, entries, objects, images, files or the like. It should be kept in mind, however, that these and similar terms are associated with appropriate physical quantities for computer operations, and that these terms are merely conventional labels applied to physical quantities that exist within and during operation of the computer.

It should be understood that manipulations within the computer are often referred to in terms such as issuing, sending, altering, adding, disabling, determining, comparing, reporting, and the like, which are often associated with manual operations performed by a human operator. The operations described herein are machine operations performed in conjunction with various inputs provided by a human operator or user that interacts with the computer.

2. Hardware

It should be understood that the programs, processes, methods, etc. described herein are not related or limited to any particular computer or apparatus, nor are they related or limited to any particular communication architecture, other than as described. Rather, various types of general purpose machines, sensors, transmitters, receivers, transceivers, and network physical layers may be used with any program modules and any other aspects of the invention constructed in accordance with the teachings described herein. Similarly, it may prove advantageous to construct a specialized apparatus to perform the method steps described herein by way of dedicated computer systems in specific network architecture with hard-wired logic or programs stored in non-volatile memory, such as read-only memory.

3. Program

In the preferred embodiment where any steps of the present invention are embodied in machine-executable instructions, the instructions can be used to cause a general-purpose or special-purpose processor which is programmed with the instructions to perform the steps of the present invention. Alternatively, the steps of the present invention might be performed by specific hardware components that contain hardwired logic for performing the steps, or by any combination of programmed computer components and custom hardware components.

The foregoing system may be conveniently implemented in a program or program module(s) that is based upon the diagrams and descriptions in this specification. No particular programming language has been required for carrying out the various procedures described above because it is considered that the operations, steps, and procedures described above and illustrated in the accompanying drawings are sufficiently disclosed to permit one of ordinary skill in the art to practice the present invention.

Moreover, there are many computers, computer languages, and operating systems which may be used in practicing the present invention and therefore no detailed computer program could be provided which would be applicable to all of these many different systems. Each user of a particular computer will be aware of the language and tools which are most useful for that user's needs and purposes.

The invention thus can be implemented by programmers of ordinary skill in the art without undue experimentation after understanding the description herein.

4. Product

The present invention is composed of hardware and computer program products which may include a machine-readable medium having stored thereon instructions which may be used to program a computer (or other electronic devices) to perform a process according to the present invention. The machine-readable medium may include, but is not limited to, floppy diskettes, optical disks, CD-ROMs, and magneto-optical disks, ROMs, RAMs, EPROMs, EEPROMs, magnet or optical cards, or other type of media/machine-readable medium suitable for storing electronic instructions. Moreover, the software portion of the present invention may also be downloaded as a computer program product, wherein the program may be transferred from a remote computer (e.g., a server) to a requesting computer (e.g., a client) by way of data signals embodied in a carrier wave or other propagation medium via a communication link (e.g., a modem or network connection).

5. Components

The major components (also interchangeably called aspects, subsystems, modules, functions, services) of the system and method of the invention, and examples of advantages they provide, are described herein with reference to the figures. For figures including process/means blocks, each block, separately or in combination, is alternatively computer implemented, computer assisted, and/or human implemented. Computer implementation optionally includes one or more conventional general purpose computers having a processor, memory, storage, input devices, output devices and/or conventional networking devices, protocols, and/or conventional client-server hardware and software. Where any block or combination of blocks is computer implemented, it is done optionally by conventional means, whereby one skilled in the art of computer implementation could utilize conventional algorithms, components, and devices to implement the requirements and design of the invention provided herein. However, the invention also includes any new, unconventional implementation means.

6. Web Design

Any web site aspects/implementations of the system include conventional web site development considerations known to experienced web site developers. Such considerations include content, content clearing, presentation of content, architecture, database linking, external web site linking, number of pages, overall size and storage requirements, maintainability, access speed, use of graphics, choice of metatags to facilitate hits, privacy considerations, and disclaimers.

7. Other Implementations

Other embodiments of the present invention and its individual components will become readily apparent to those skilled in the art from the foregoing detailed description. As will be realized, the invention is capable of other and different embodiments, and its several details are capable of modifications in various obvious respects, all without departing from the spirit and the scope of the present invention. Accordingly, the drawings and detailed description are to be regarded as illustrative in nature and not as restrictive. It is therefore not intended that the invention be limited except as indicated by the appended claims.

What is claimed is:

1. A computer implemented method for predicting properties of lubricant base oil blends, comprising the steps of:
   a. generating an NMR spectrum, HPLC-UV spectrum, and FIMS spectrum of a sample of a blend of at least two lubricant base oils;
   b. determining at least one composite structural molecular parameter of the sample from said spectrums;
   c. generating SIMDIST and HPO analyses of the sample;
   d. determining a composite boiling point distribution and molecular weight of the sample from such analysis;
   e. applying the at least one composite structural molecular parameter, the
   composite boiling point distribution and the composite molecular weight to a
   trained neural network trained to correlate with the at least one composite structural molecular parameter, the composite boiling point distribution and the composite molecular weight so as to predict composite properties of the sample, wherein the properties comprise Kinematic Viscosity at 40 C, Kinematic Viscosity at 100 C, Viscosity Index, Cloud Point, and Oxidation Performance.

2. The computer implemented method of claim 1, further comprising steps of providing a neural network and training said neural network so as to provide said trained neural network.

3. The computer implemented method according to claim 2, wherein said training step comprises the steps of:
   a. obtaining a set of lubricant base oil samples;
   b. generating NMR, HPLC-UV, and FIMS spectra and SIMDIST and VPO data for said set of hydrocarbon samples;
   c. measuring desired properties, comprising Kinematic Viscosity at 40 C, Kinematic Viscosity at 100 C, Viscosity Index, Cloud Point, and Oxidation Performance, of said set of the lubricant base oil samples so as to provide known properties;

d. determining at least one structural molecular parameter, the boiling point distribution and the molecular weight of each of the lubricant base oil samples;
e. for each known lubricant base oil property, building a matrix of at least one structural molecular parameter, the boiling point distribution and the molecular weight and known property for the set of lubricant base oil samples, thereby resulting in a model for each lubricant base oil property; and
f. training the neural network with the at least one structural molecular parameter, the boiling point distribution and the molecular weight and each lubricant base oil property matrix to obtain a correlation between the at least one structural molecular parameter, the boiling point distribution and the molecular weight inputs and lubricant base oil properties outputs, so as to provide said trained neural network.

* * * * *